United States Patent [19]

Okonogi et al.

[11] 4,418,070

[45] Nov. 29, 1983

[54] CARDIOTONIC AGENTS

[75] Inventors: Tsuneo Okonogi, Yokohama; Shunzo Fukatsu; Mitsugu Hachisu, both of Tokyo; Hiroko Kawashima, Yokohama; Keiko Shitoh, Kawasaki; Yasuharu Sekizawa, Tokyo, all of Japan

[73] Assignee: Meiji Seika Kabushiki Kaisha, Tokyo, Japan

[21] Appl. No.: 345,672

[22] Filed: Feb. 4, 1982

[30] Foreign Application Priority Data

Feb. 14, 1981 [JP] Japan ................................ 56-20490

[51] Int. Cl.³ ............................................ C07D 277/34
[52] U.S. Cl. ................................... 424/270; 548/182
[58] Field of Search ......................... 424/270; 548/182

[56] References Cited

PUBLICATIONS

Bolt, Biochem. Pharm. 23, 1969 (1974).
Aldrich, Catalog, p. 83, 1982.
Kikuchi et al., Nippon Suisan Gakkaishi, 40, 325 1974, Abstract Only.

*Primary Examiner*—Robert Gerstl
*Attorney, Agent, or Firm*—Oblon, Fisher, Spivak, McClelland & Maier

[57] ABSTRACT

A 5-phenylthiazole derivative represented by the formula:

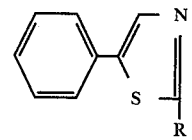

wherein R represents a hydrogen atom, a lower alkyl group, a hydroxyl group, an amino group or a mercapto group, or a pharmaceutically acceptable salt thereof shows a cardiac effect and a low toxicity to a human or animal with little influence on atrium rhythms.

11 Claims, No Drawings

CARDIOTONIC AGENTS

BACKGROUND OF THE INVENTION

This invention relates generally to cardio stimulants or cardiotonic agents. More particularly, the present invention pertains to a novel cardiac composition containing a specific 5-phenylthiazole derivative as active ingredient.

We have previously reported on pharmacological analytical research concerning 4-phenylthiazole type compounds (J. Pharm. Dyn. 3, 85–93, 1980). As a result of further progress of the research, it has been found that 5-phenylthiazoles have novel pharmacological properties. More specifically, according to our discovery, as contrasted to 4-phenylthiazoles which generally inhibit the force of systolic contraction of specimens of the atrial muscle depending on the dosages administered, 5-phenylthiazoles markedly increase the force of systolic contraction of specimens of the atrial muscle according to the dosages administered.

SUMMARY OF THE INVENTION

The present invention is based on our above finding and has been accomplished as the result of preparation of 5-phenylthiazoles according to organic synthesis and investigations on cardiac properties thereof.

The cardiotonic agent according to the present invention is characterized by containing as an active ingredient a 5-phenylthiazole derivative represented by the formula shown below or a pharmaceutically acceptable salt thereof.

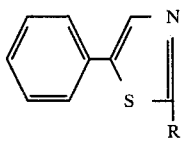

(I)

wherein R represents a hydrogen atom, a lower alkyl group (preferably one containing up to 4 carbon atoms), a hydroxyl group, an amino group, or a mercapto group.

The present invention, according to another aspect thereof, provides a pharmaceutical composition useful in the treatment of cardiac failure conditions comprising a safe and effective amount of the above 5-phenylthiazole derivative or a pharmaceutically acceptable salt thereof and a pharmaceutically acceptable carrier.

The present invention further provides a method for treating cardiac failure conditions comprising administering to a human or animal in need of such treatment a safe and effective amount of the above 5-phenylthiazole derivative or a pharmaceutically acceptable salt thereof and a pharmaceutically acceptable carrier thereof.

DETAILED DESCRIPTION OF THE INVENTION

1. 5-Phenylthiazole derivatives

The compounds to be used in the present invention are 5-phenylthiazole derivatives represented by the above formula (I) and pharmaceutically acceptable salts thereof. Non-limiting examples of such salts are acid addition salts such as those of hydrochloric acid, hydrobromic acid, sulfuric acid, succinic acid, malic acid, etc. Among them, hydrochlorides and hydrobromides are particularly preferred.

Of these compounds, thiazoles having phenyl group at the 5-position of the thiazole ring and hydrogen, methyl group, amino group or mercapto group at the 2-position are known compounds and disclosed in various publications and Patent specifications as hereinafter mentioned.

The compounds of the formula (I) can be synthesized according to the methods described in Heterocyclic Compound, Vol. 34, part 1 (John Wiley & Sons) and other publications. For example, a thiazole ring may be formed by the reaction of an α-haloketone with thioamide, thiourea or thiocarbamate. Such a reaction is generally carried out by, if necessary, blocking with conventional blocking groups the hydroxyl, amino or sulfonic acid groups which do not particpiate in the reaction, before causing cyclization reaction. Typical examples of synthetic methods are described below.

In synthesis of 5-phenylthiazole derivatives, the intermediate α-bromo-α-phenylacetaldehyde is first synthesized by allowing phenylacetaldehyde to react with bromine according to the method as disclosed in Helv. Chim. Acta. Vol. 30, pp.2058 (1945). As the next step, according to the method disclosed in J. Amer. Chem. Soc. Vol. 71, pp.4007 (1949), α-bromo-α-phenylacetaldehyde is allowed to react respectively with thioformaldehyde, thioacetamide, thiourea and ethylthiocarbamate at room temperature in methanol as a reaction solvent to obtain 5-phenylthiazole (m.p. 45°–46° C.), 2-methyl-5-phenylthiazole (m.p. 74°–76° C.), 2-amino-5-phenylthiazole (m.p. 206°–208° C.) and 2-hydroxy-5-phenylthiazole (m.p. 202°–204° C.). On the other hand, according to the method as described in U.S. Pat. No. 2,603,646 (1952), phenylacetaldehyde is allowed to react with thiocyanogen to obtain α-phenyl-α-thiocyanoacetaldehyde, which is then allowed to react with ammonium dithiocarbamate in the presence of an acid catalyst such as dilute sulfuric acid to obtain 2-mercapto-5-phenylthiazole (m.p. 207°–209° C.).

Of these compounds, 2-hydroxy-5-phenylthiazole is a novel substance.

2. Physiological activity (1) Cardiac effect:

The compounds of the formula exhibit excellent cardiac effect as described in detail below.

A. Effect on isolated atrial muscle specimens of rats (1) Experimental method (Magnus method)

The heart was isolated by thoracotomy of a Wistar rat under ether anesthesia and placed in a Krebs-Henseleit solution to separate the atrium from the ventricle. The atrium was suspended in an organ bath filled with the Krebs-Henseleit solution (35±1° C.) saturated with a gas mixture of 95%$O_2$+5%$CO_2$ for measurement of the force of systolic contraction of the atrial muscle and atrial rate. The contraction force was recorded through a tension transducer, and the atrial rate through a tachometer, respectively, on a multi-purpose monitor recording device (Pen-Wrigthing Oscillo Graph). The compounds (drugs) to be tested were added into the organ bath.

(2) Results

Marked increase in contraction force of the atrial muscle was observed when a 5-phenylthiazole derivative was present in an amount ranging from $10^{-6}$ g/ml to $10^{-4}$ g/ml, while little influence was observed on atrial rate. Such properties may be said to be by far superior to the cardiac effect of theophylline.

The results shown in Tables 1 and 2 indicate the change rates in forces of contraction and in atrial rates, respectively, which are obtained by dividing the maximum difference in values between those obtained after and before the addition of the drugs with the values before addition, and which are represented as (+) in case of increase and as (−) in case of decrease in terms of percentage of changes. The values in the Tables indicate average values of change rates (%) ± standard errors (number of test animals: 5).

TABLE 1

Effect on force of contraction of isolated atrial muscle of rat

| Compound | Concentration of drug in bath (g/ml) | | | |
|---|---|---|---|---|
| | $3 \times 10^{-6}$ | $1 \times 10^{-5}$ | $3 \times 10^{-5}$ | $1 \times 10^{-4}$ |
| 1. (structure: phenyl-CH=C(S)(N) ring) | | | | +49.3 ±4.7 |
| 2. (structure with OH) | | | +38.3 ±12.7 | +124.1 ±29.3 |
| 3. (structure with HCl, NH₂) | | +57.1 ±16.7 | +111.3 ±23.1 | |
| 4. (structure with CH₃) | | | | +82.4 ±19.7 |
| 5. Theophylline | | | | +43.7 ±12.1 |

Note:
Preparation of drugs to be tested: Compounds 1, 3, and 5 were used as suspensions in distilled water, and the Compounds 2 and 4 as suspensions in Nikkol HCO 60.

TABLE 2

Effect on atrial rate of isolated atrial muscle of rat

| Compound | Concentration of drug in bath (g/ml) | | | |
|---|---|---|---|---|
| | $3 \times 10^{-6}$ | $1 \times 10^{-5}$ | $3 \times 10^{-5}$ | $1 \times 10^{-4}$ |
| 1. (structure) | | | | −19.7 ±5.7 |
| 2. (structure with OH) | | | −3.6 ±2.3 | −6.2 ±4.9 |

TABLE 2-continued

Effect on atrial rate of isolated atrial muscle of rat

| Compound | Concentration of drug in bath (g/ml) | | | |
|---|---|---|---|---|
| | $3 \times 10^{-6}$ | $1 \times 10^{-5}$ | $3 \times 10^{-5}$ | $1 \times 10^{-4}$ |
| 3. (structure with HCl, NH₂) | | +22.9 ±14.2 | +33.8 ±10.2 | |
| 4. (structure with CH₃) | | | | +2.2 ±10.8 |
| 5. Theophylline | | | | +23.5 ±5.6 |

The above results show the potent characteristics as cardiotonic agent of the compounds of the formula (I).

B. Effect on the cardiovascular systems of dogs (1) Experimental method

Three beagles weighing 11 to 12 kg were anesthetized by intravenous injection of 20 mg/Kg of pentobarbital sodium. After a cannula was inserted into the trachea of each dog, thoracotomy was mesially operated to expose the heart while practicing artificial respiration at 20 ml/Kg and 20 strokes/min. The force of contraction of the right ventricle was measured by a contractility pick-up (Nippon Koden K.K.; TH-602T) attached by suture to the surface of the right ventricle, the carotid blood pressure by insertion of a cannula into the left arteria carotis communis, the quantities of blood flow through ascending aorta and femoral artery by mounting of probes for measurement of blood circulations respectively at blood vessels to be connected to an electromagnetic flowmeter (Nippon Koden K.K.; MF-26) and the heart rates through a tachometer, each measuring means being connected to a multipurpose monitor recording device (Nippon Koden K.K.; RM-85) to carry out simultaneous recording. Electrocardiograms (I, II and III induction) were recorded by using a terminal device for collecting electrocardiograms for 3-channels (Nippon Koden K.K.; DEC-3323). In order to maintain the depth of anesthesia as constant as possible, pentobarbital sodium was continuously injected into the left femoral artery at a dosage of 5 mg/Kg per hour. The drugs to be tested were injected as isotonic sodium chloride solutions into the right femoral vein when the animals were under stable conditions. The results were observed with each of the items shown in Table 3. The measurement values in the Table show the difference between the peak value of the response after administration and the average value before administration.

(2) Results

TABLE 3

Effect of 2-amino-5-phenylthiazole on cardiovascular system of dog

| Items of observation | Drugs to be tested | |
|---|---|---|
| | 2-amino-5-phenyl-thiazole dose: 1 mg/Kg | theophylline dose: 5 mg/Kg |
| Blood pressure (mm Hg) | → | 27 ↓ Diastolic blood pressure ↓ * |
| Blood flow through femoral artery (ml/min.) | → | 10 ↑  20 ↓  20 ↑ |
| Heart rates (beats/min.) | 32 ↑ | 20 ↑ |
| Blood flow through ascending aorta (liter/min.) | 0.2 ↑ | 0.15 ↓ |
| Force of systolic contraction (%) | 107 ↑ | 53 ↑ |

Notes:
(1) The indications of the arrow marks are as follows.
↑ : elevation or increase;
↓ : downfall or decrease;
→: no change.
(2) *: The three values indicated by * mean the differences at the response peaks appearing with elapse of time (see the item of (2)-2 Theophylline shown below about its details).

(2)-1 2-Amino-5-phenylthiazole:

As shown in Table 3, substantially no change in blood pressure and quantity of blood flow through the femoral artery was observed, but the blood flow through the ascending aorta was increased by 0.2 liter/min., and the force of systolic contraction increased by 107%. Other than the quantities in Table 3, the T-wave in the electrocardiodiagram showed a tendency to be increased. Each of these changes disappeared after 5 minutes.

(2)-2 Theophylline:

Blood pressure was lowered by 27 mmHg, lowering of the diastolic blood pressure being especially marked, whereby the amplitude of the blood pressure was increased. These changes disappeared and the values were restored as before after 5 minutes. The blood flow through the femoral artery was increased during administration by 10 ml/min., reduced by 20 ml/min. on termination of administration, and thereafter increased again by 20 ml/min. after 3 minutes to reach the peak, which was followed by restoration to substantially the original value after 10 minutes. The blood flow through the ascending aorta was reduced by 0.15 liter/min., but was substantially restored after 3 minutes. The force of systolic contraction was increased by 53%. On the electrocardiodiagram, the T-wave showed a tendency to be increased but was restored after 5 minutes.

As described above, the compound of the present invention may be said to be superior to theophilline in the effect on the force of systolic contraction also in the test using dogs.

(2) Toxicity:

The toxicity of the compound to be used in the present invention was evaluated with respect to 2-amino-5-phenylthiazole hydrochloride.

More specifically, when the test compound was administered intravenously to a group of six ICR-strain mice (male, six weeks of age, body weight: 25 g), all mice were alive at the level of 20 mg/Kg of 2-amino-5-phenylthiazole hydrochloride, indicating that the compound to be used in the present invention is low in toxicity. These experimental results relating to pharmacological activity suggest that the 5-phenylthiazole derivatives are clinically useful as cardiotonic agents.

3. Cardiotonic agents

The cardiotonic agent according to the present invention may be employed by suitable administration metods.

In preparation of injections, the above principal medicine may be incorporated with pH controllers, buffers, stabiliziers or isotonic agents, and the mixture may be dissolved in distilled water for injection, thus giving injections for intravenous administration according to conventional methods.

In the case of preparation of solid preparations, the principal medicine may be incorporated with conventional excipients, stabilizers and further, if desired, binders, vehicles, lubricants, colorants, taste modifiers, etc. Then, following conventional procedures, tablets, coated tablets, granules, powders, capsules, etc. may be formed. The cardiotonic agent according to the present invention may also contain other cardiotonic agents or other drugs so far as they are compatible with the compound of the formula (I).

The cardiotonic agent of the present invention may be administered in a dose which should adequately be determined by the attendant physician depending on the specific case. To show a typical example of dosage in the case of 2-amino-5-phenylthiazole hydrochloride, the daily dose per human adult, which may differ depending on the body weight, age, severity of disease, etc. may be generally 5 mg to 0.5 g, which may be applicable either as an intravenous or oral administration.

4. Examples

The following Examples are set forth only for illustration of the methods for preparation of various preparations, it being understood that the present invention is not limited at all by these Examples.

EXAMPLE 1

Five (5) grams of 2-amino-5-phenylthiazole hydrochloride and 5 g of mannitol are dissolved in distilled water to form 1,000 ml of a solution. The solution is sterilized according to conventional procedure and apportioned into lots each of 2 ml in vials. This step is then followed by lyophilization. This preparation is diluted with distilled water for injection into an injection solution before use.

EXAMPLE 2

One part of 2-hydroxy-5-phenylthiazole and 4 parts of lactose are thoroughly blended, and the mixture is screened through a 50-mesh screen to provide a powder.

EXAMPLE 3

One part of 2-methyl-5-phenylthiazole, 2.7 parts of lactose, 0.8 part of corn starch and 0.05 part of polyvinyl pyrrolidone are mixed together and granulated with ethanol according to conventional procedure, dried and classified into uniform sizes. The resultant granules are mixed with 0.5% of magnesium stearate and formed in a conventional manner into tablets each of 100 mg.

What is claimed is:

1. A method for treating cardiac failure conditions, comprising:
   administering to a human or animal in need of such treatment a safe and effective amount of a 5-phenylthiazole derivative represented by the formula:

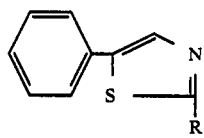 (I)

wherein R represents a hydrogen atom, a lower alkyl group, a hydroxyl group, an amino group, or a mercapto group, or a pharmaceutically acceptable salt thereof.

2. The method of claim 1, wherein said amount is from about 5 mg to about 0.5 g per day.

3. The method of claim 1, wherein said derivative is 2-amino-5-phenylthiazole or a pharmaceutically acceptable salt thereof.

4. The method of claim 1, wherein the pharmaceutically acceptable salt is an acid addition salt of the 5-phenylthiazole derivative with an acid selected from the group consisting of hydrochloric acid, hydrobromic acid, sulfuric acid, succinic acid, and malic acid.

5. The method of claim 1, wherein said derivative is 2-hydroxy-5-phenylthiazole.

6. The method of claim 1, wherein said derivative is administered in a pharmaceutical composition comprising said derivative and a pharmaceutically acceptable carrier.

7. The method of claim 1, wherein said composition is in tablet form.

8. The method of claim 1, wherein said composition is in liquid form.

9. The method of claim 1, wherein said derivative is administered orally.

10. The method of claim 1, wherein said derivative is administered intraveneously.

11. 2-Hydroxy-5-phenylthiazole.

* * * * *